(12) United States Patent
Shimchuk et al.

(10) Patent No.: US 8,295,916 B2
(45) Date of Patent: Oct. 23, 2012

(54) AUTOMATED STRONTIUM-RUBIDIUM INFUSION SYSTEM

(75) Inventors: Gennady Grigoryevich Shimchuk, Moscow (RU); Gennady Arkadyevich Pakhomov, Moscow (RU); Grigory Gennadyevich Shimchuk, Moscow (RU); Aleksei Borisovich Utenkov, Moscow (RU); Valery Timofeevich Galochkin, Moskovskaya oblast (RU); Aleksandr Vladislavovich Ogurtsov, Moscow (RU); Valery Ivanovich Kostuchenko, Moscow (RU)

(73) Assignee: OOO 'Nauchno Proizvodstvennaya Firma "Pozitom-Pro", Moscow (RU)

( * ) Notice: Subject to any disclaimer, the term of this patent is extended or adjusted under 35 U.S.C. 154(b) by 504 days.

(21) Appl. No.: 12/545,605

(22) Filed: Aug. 21, 2009

(65) Prior Publication Data

US 2009/0312635 A1    Dec. 17, 2009

Related U.S. Application Data

(63) Continuation of application No. PCT/RU2008/000211, filed on Apr. 4, 2008.

(30) Foreign Application Priority Data

Apr. 9, 2007    (RU) ................................ 2007113009

(51) Int. Cl.
*A61B 6/00*    (2006.01)
(52) U.S. Cl. .......................... 600/436; 588/249; 588/260
(58) Field of Classification Search .................. 600/436; 588/249, 260
See application file for complete search history.

(56) References Cited

U.S. PATENT DOCUMENTS

| | | | | |
|---|---|---|---|---|
| 4,562,829 A |   | 1/1986 | Bergner | |
| 5,113,868 A | * | 5/1992 | Wise et al. | 600/488 |
| 6,006,588 A | * | 12/1999 | Cartwright et al. | 73/49.2 |
| 2005/0278066 A1 | * | 12/2005 | Graves et al. | 700/239 |

FOREIGN PATENT DOCUMENTS

| | | |
|---|---|---|
| EP | 0310148 A2 | 4/1989 |
| RU | 2219959 C2 | 12/2003 |

OTHER PUBLICATIONS

International Search Report, mailed Sep. 4, 2008, from International Application No. PCT/RU2008/000211, filed on Apr. 4, 2008.

* cited by examiner

*Primary Examiner* — Brian Casler
*Assistant Examiner* — Daniel Huntley
(74) *Attorney, Agent, or Firm* — Patentbar International, P.C.

(57) ABSTRACT

The strontium-rubidium infusion system has a container with eluent, a strontium-rubidium generator with a filter and pressure sensor, an eluate infusion unit, which are connected via a transporting system having pipes and two three-way valves, radioactivity measuring means and a control and operating unit. An eluent container is connected to a syringe pump via the first and second ports of the first three-way valve, the first port of the second three-way valve is connected with pipes via the second filter to the eluate infusion unit, the second port is connected to a waste receptacle. The third and fourth three-way valves, the first and second air bubbles detectors are connected to the control and operating unit connected with a computer. The third three-way valve is connected with its first and second ports via pipes to the third port of the first three-way valve and the input of the generator, respectively.

7 Claims, 3 Drawing Sheets

AUTOMATED STRONTIUM-RUBIDIUM INFUSION SYSTEM

RELATED APPLICATIONS

This application is a Continuation of International Application No. PCT/RU2008/000211, filed on Apr. 4, 2008, which claims priority to Russian Patent Application No. 2007113009, filed on Apr. 9, 2007, both of which are incorporated herein by reference in their entirety.

FIELD OF THE INVENTION

The invention relates to medical engineering, in particular, to means of automation of the process of generating a diagnostic solution from a radionuclide strontium-rubidium generator and performing of remote controlled infusion, with automatic control over the key characteristics of the process, such as the value of introduced activity, the value of occlusion, availability of air bubbles, as well as the weight and activity of solution in a waste container.

BACKGROUND OF THE INVENTION

One of the most promising fields of nuclear diagnostics is positron emission tomography (PET). These are short-lived and ultra-short-lived isotopes, such as C-11, O-15, N-13, F-18, that are used for work at PET centers. This imposes a requirement to have cyclotrons for generation of such isotopes on the site of diagnostics. Opportunities of PET diagnostics may be considerably expanded with use of generator systems, where the life time of parent radionuclide is much longer than the life time of radionuclides generated on cyclotrons of PET centers. Among the isotope generators for PET, the most promising are generator systems
$^{82}Sr(t_{1/2}=25.6\ days) \rightarrow ^{82}Rb(t_{1/2}=75\ sec)$ and $^{68}Ge(t_{1/2}=271\ days) \rightarrow ^{68}Ga(t_{1/2}=68.3\ min)$.

Therefore, as applied to generator isotopes, one may consider procurement of them to any clinics equipped with PET scanners, within a region, a nation, or a group of nations.

Generator systems may find the most common application in the so-called mobile PET units mounted in trailers, which are called for servicing clinics not equipped with PET scanners, let alone their own cyclotrons. The fact that such a mobile PET scanner is not "tied" to an isotope base enlarges considerably the range of an area it caters for.

There is known a strontium-rubidium infusion system for generation of diagnostic solution from a radionuclide strontium-rubidium generator and performing controlled infusion (U.S. Pat. No. 4,562,829, 1986), which comprises a container with eluent connected to a syringe pump with relevant pipes of the transporting system via the first three-way valve, a strontium-rubidium generator with the first filter and a pressure sensor at the input, the second three-way valve, its first port connected via the second filter to a unit for eluate infusion into a patient, and its second port connected to means of collection and storage of excessive eluate, radioactivity measuring means, and a control and operating unit. The known system is not perfect in terms of both protection from nuclear radiation and service life of the generator column.

SUMMARY OF THE INVENTION

The claimed invention is aimed at elimination of the aforesaid shortcomings. The technical result obtained with its application lies in higher efficiency of diagnostic procedure owing to automation of the infusion procedure, reducing the dosage of undesirable nuclear radiation affecting the patient and the operating personnel, and extension of the service life of the generator column.

The essence of the claimed invention lies in the fact that an automated strontium-rubidium infusion system comprises a container with eluent, a strontium-rubidium generator with a filter and a pressure sensor at the input, a unit for eluate infusion into a patient, which are connected by means of a transporting system provided with pipes and two three-way valves, radioactivity measuring means, and a control and operating unit. Here, an eluent container is connected to a syringe pump via the first and second ports of the first three-way valve, the first port of the second three-way valve is connected with pipes via the second filter to the unit for eluate infusion into a patient, and the second port is connected to a waste receptacle. The system additionally comprises the third and fourth three-way valves, the first and second air bubbles detectors are connected to the control and operating unit connected with a computer, where the third three-way valve is connected with its first and second ports via pipes to the third port of the first three-way valve and the input of the strontium-rubidium generator, respectively. The generator output is connected to the first port of the fourth three-way valve, where the third port of the third valve and the second port of the fourth valve are connected with a pipe, the first air bubbles detector is placed on the pipeline between the eluent container and the first port of the first valve, and the second air bubbles detector is placed on the pipeline between the third ports of the fourth and second valves.

Besides, the radioactivity measuring means comprise the first and second first and second activity sensors. Here, the first activity sensor is placed in the pipeline between the third ports of the fourth and second valves and is implemented in the form of a beta-ray detector.

Radiation protection of means for collection and storage of excessive eluate may be implemented in the form of a protective box comprising waste weight control means implemented in the form of a force sensor, with the second activity sensor placed in the port of the protective box for determination of the waste radioactivity, in the form of a gamma-ray detector.

The column of the strontium-rubidium generator has radiation protection comprising, preferably, an external primary protective container and a protective shipping container, where the primary protective container is fixed on the rack of a trolley.

The system is installed in a closed movable housing. Besides, the housing is provided with a sliding tabletop.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

Figure 1:
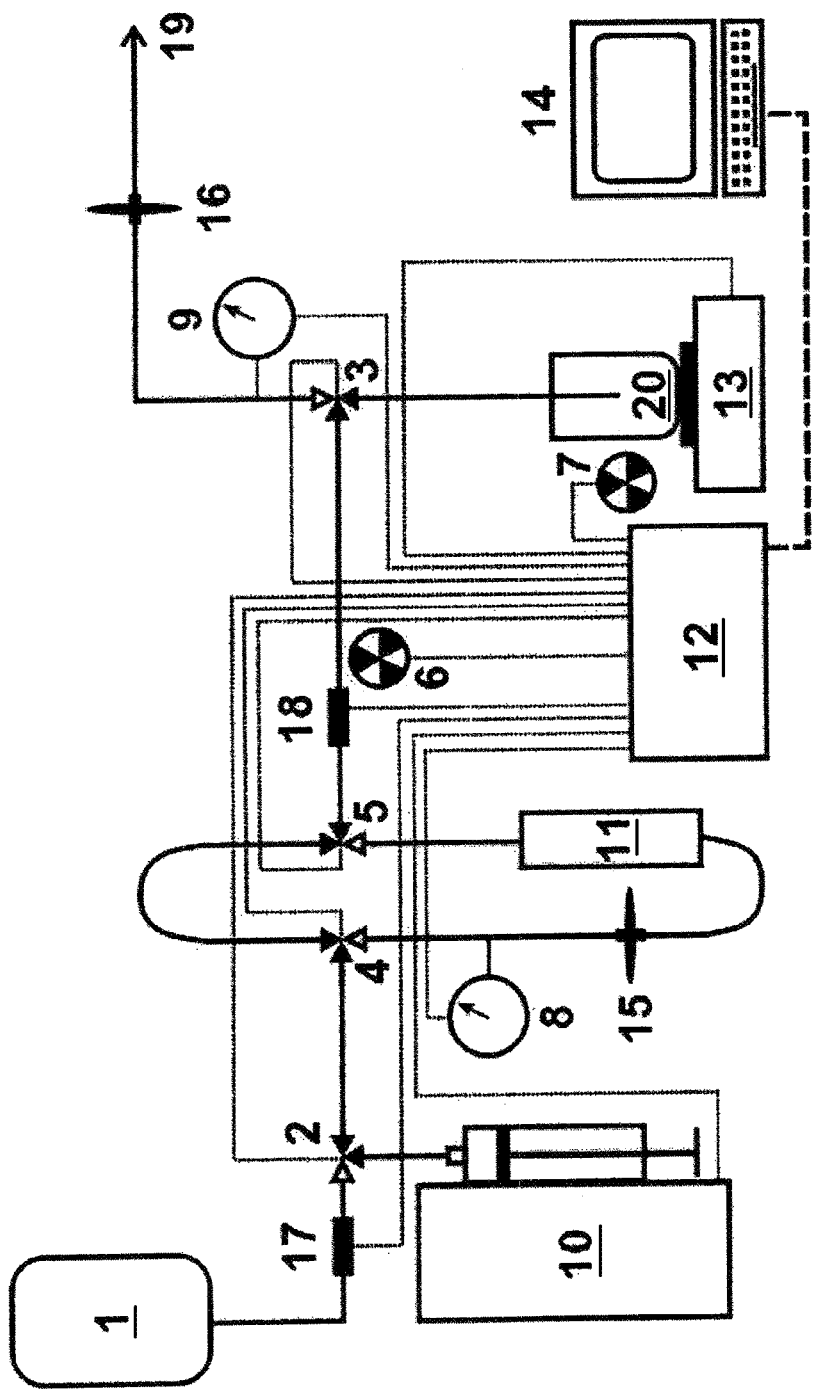
FIG. 1 presents the layout of infusion system.

Below are specified conventions used in the drawing:

1 is eluent container
2, 3, 4, 5 are three-way valves
6, 7 are activity sensors
8, 9 are pressure sensors
10 is syringe pump
11 is strontium-rubidium generator
12 is control and operating unit
13 is weight sensor
14 is remote computer
15, 16 are filters
17, 18 are air bubbles detectors
19 is unit (needle) for eluate infusion into a patient
20 is eluent and eluate waste receptacle
21 is movable housing
22 is stand
23 is protective container of strontium-rubidium generator
24 is protective container for beta-ray detector
25 is power supply
26 is protective box for waste container
27 is moving tabletop.

DETAILED DESCRIPTION OF THE PREFERRED EMBODIMENTS

Figure 2:
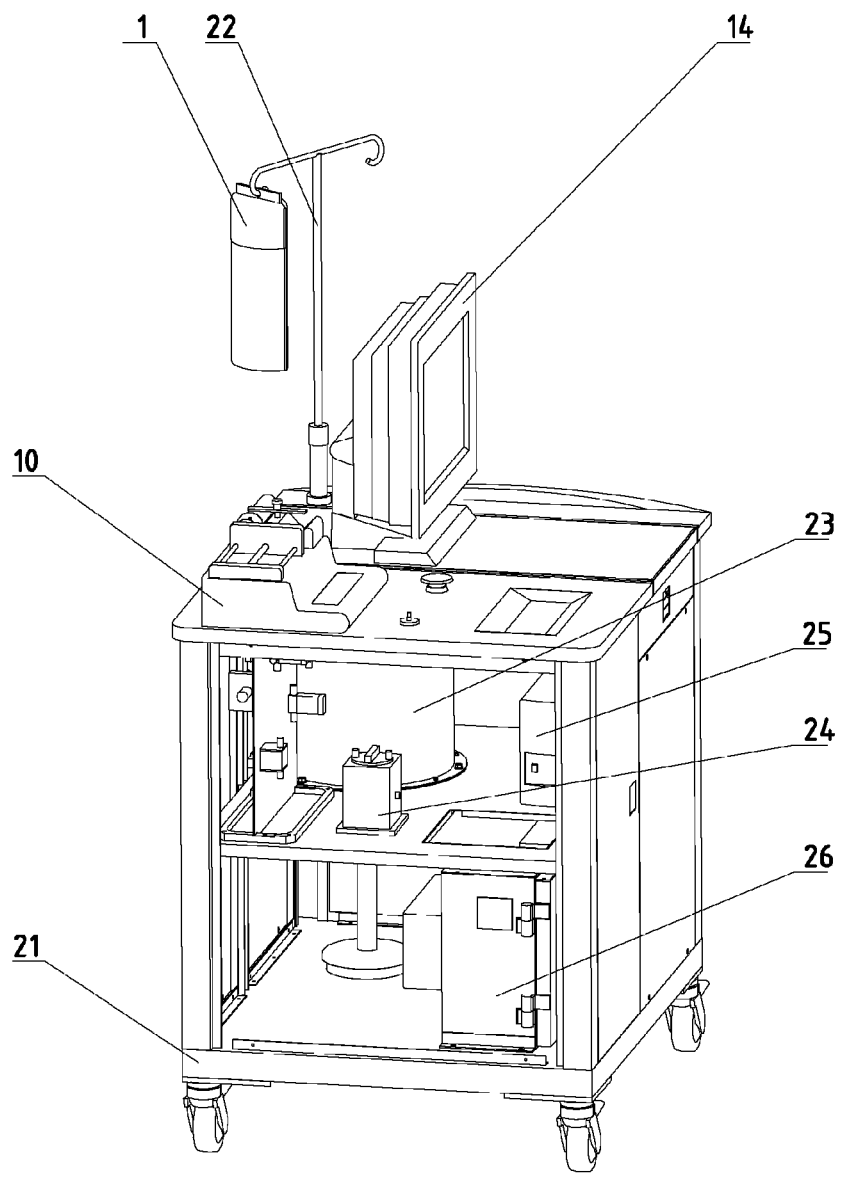
FIG. 2 presents the general side view of generator unit.

The automated strontium-rubidium infusion system comprises means for generation of rubidium-82 in a solution, which may be administered into the patient, namely, strontium-rubidium generator 11 (FIG. 1) of a standard type in a shipping container. This container is placed inside protective external primary container 23 and, jointly with the latter one, performs the function of primary radiation protection. The assembled system may be installed in movable housing 21 (FIG. 2) closed with decorative panels (not shown). There is stand 22 mounted on the tabletop, with eluent container 1 fixed on the stand. Besides, here is also placed syringe pump 10 and computer 14. On the upper rack of movable housing 21, there are installed:

primary protective container 23, which accommodates a standard shipping container with strontium-rubidium generator 11;
protective box 24, which accommodates a beta-activity detector measuring the activity of the solution, which has passed through the strontium-rubidium generator;
power supply 25.

On the lower rack, there is placed protective box 26, which accommodates a receptacle for eluent and eluate waste.

Figure 3:
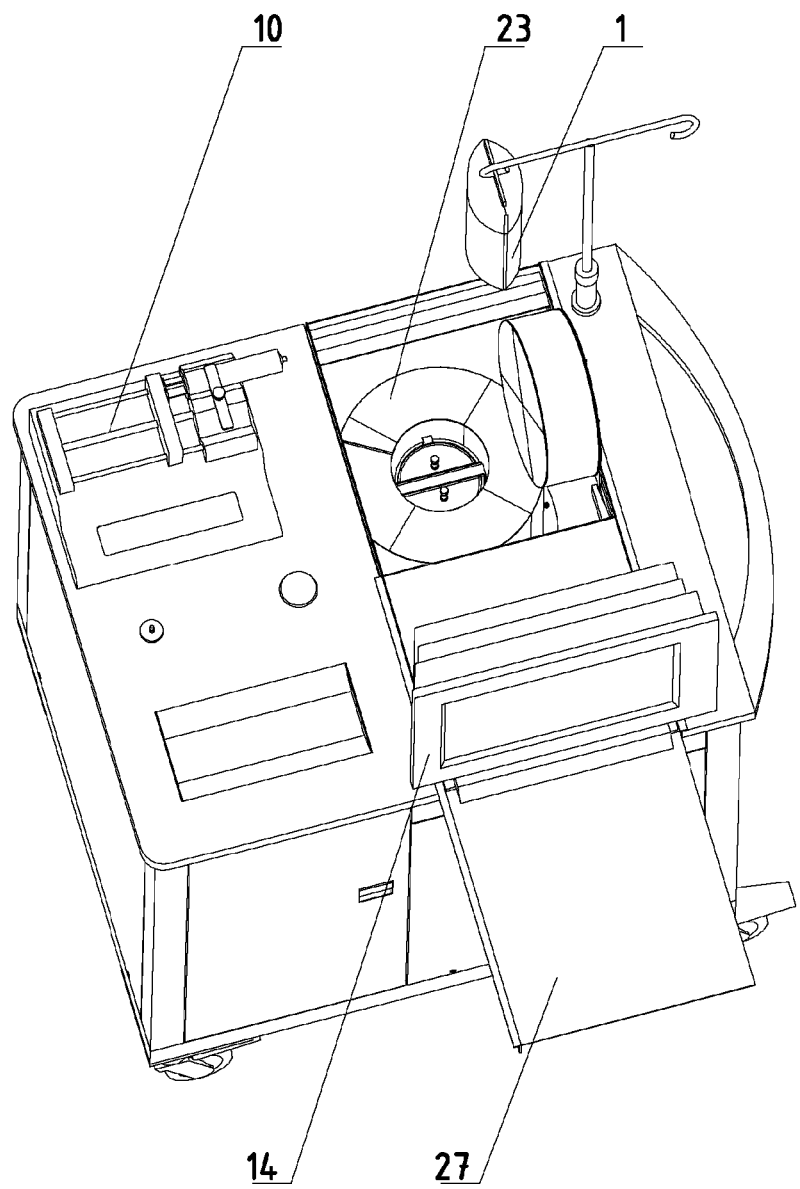
FIG. 3 presents the general view of generator unit from above.

In FIG. 3, the upper lid of container 23 is opened, which makes visible a cavity housing the shipping container with strontium-rubidium generator 11. To facilitate an access to primary protective container 23 during recharging of the generator system (the shipping container with a used column of strontium-rubidium generator 11 is removed, and a shipping container with a fresh generator column is installed), a part of the tabletop is implemented in the form of sliding tabletop 27, which ensures more comfortable operation.

In addition, the system comprises means for performing infusion, namely, (FIG. 1): remotely controlled syringe infusion pump 10, its rod set in operation, e.g., with a stepping motor; means for automated filling of the syringe pump with eluent 1 (0.9% solution of NaCl); system of eluent and eluate transportation to the patient, or receptacle of eluent and eluate waste provided with multi-way (three-way) valves 2-5 (FIG. 1), which exercise ramification of the transporting system subject to a program of operations; antibacterial protection means, namely, antibacterial filters 15 and 16 at the input and output of the transporting system; means for measuring the eluate activity for current control and dosing in the course of infusion into the patient 6 and 7; means for measuring pressure 8 and 9 in the transporting system, including those for measuring occlusion; receptacle for eluent and eluate waste 20, including those providing measuring of the activity value and weight of the solution in waste container 13 and exercising protection from radioactivity; means for automated control over the overall elution process and its components 12, exercised by means of onboard or remote computer 14.

In the system under consideration, eluent (salt solution) container 1 is connected with plastic fitting to pipe (e.g., an infusion tube, which has an outer diameter of 2.5 mm and an inner diameter of 1.5 mm). Sections of such pipes (pipelines) are further used for construction of the entire transporting system for infusion. The other end of the pipeline is connected via air bubbles detector 17, which, in case of passage of an air bubble, generates a signal to control and operating unit 12, which generates a control signal to valves 2, 3, 4 and 5, as a result of which the eluent solution containing an air bubble is removed to receptacle for eluent and eluate waste 20, without passing the column of strontium-rubidium generator 11.

Valve 2 performs switching of the infusion system to one of two possible operating modes: (1) filling the syringe, with syringe pump 10 operating for suction of the salt solution from eluent container 1 (via the first and second ports of the valve) or (2) infusion, i.e. delivery of salt solution from the filled syringe of syringe pump 10 into the infusion system (via the first and second ports of the valve).

Three-way valve 2 is further connected with a section of connecting pipe to the first port of third three-way valve 4, its second port connected via filter 15 to the input of the column of strontium-rubidium generator 11. Control of pressure at the input of the column of strontium-rubidium generator 11 is exercised by first pressure sensor 8.

Valve 4 is connected with its third port, via a section of connecting pipe, to the second port of fourth three-way valve 5. This valve also has connections to the output pipe of the column of strontium-rubidium generator 11 (first port) and extension of the infusion system on the third port.

In the infusion operating mode of the syringe pump, the pair of three-way valves 4, 5, operating synchronously, allow either pumping the salt solution from syringe 10 through the column of strontium-rubidium generator further to the infusion system, already as eluate, i.e., solution enriched with Rb-82, or pumping the salt solution into the infusion system by-passing strontium-rubidium generator 11. This operating mode is used, when the required amount of activity of Rb-82 is generated and must be delivered to patient through eluate infusion unit 19, and the infusion system must be filled with inactive salt solution by the end of infusion into the system. In the mode of pumping of salt solution, virtually the entire infusion system, except for the connecting pipeline from the output of the strontium-rubidium generator to the fourth three-way valve, will be filled with non-radioactive salt solution and will not act as a source of additional undesirable radioactivity affecting the patient and the operating personnel; besides, the volume of salt solution required to force the rest of the generated eluate into the patient will not pass through the column of the strontium-rubidium generator and exhaust it, as the generator's potential is known to depend not only on the period of its operation, but also on the volume of salt solution passed through it.

On the pipeline from the third port of fourth three-way valve 5 to the third port of second three-way valve 3, there are installed first radioactivity detector 6 (beta-ray detector) and second air bubbles detector 18 similar to first air bubbles detector 17. On detection of an air bubble, detector 18 generates a signal to the control and operating unit, which generates a control signal to the port of second three-way valve 3. As a result, the eluate containing an air bubble is removed to receptacle for eluent and eluate waste 20. If no air bubble has been detected, the eluate is fed through the first port of three-way valve 3 and second filter 16 into the patient, i.e., to needle 19.

Radioactivity detector 6 operates in real time and measures activity of Rb-82 at location of detector 18.

Control over filling of the waste receptacle with liquid is exercised by means of a force sensor (not shown). Second radioactivity sensor 7 (gamma-ray detector) is used for measuring radioactivity contained in the receptacle for eluent and eluate waste. Radiation protection of the means for collection and storage of excessive eluate is implemented in the form of a protective box, which comprises a force sensor, with the second activity sensor placed in the port of the protective box.

In the course of infusion into the patient, second three-way valve 3 is switched to passing eluate to the pipeline connected to needle 19 via Millipore filter 16. This section is provided with second pressure sensor 9, which allows measuring of occlusion pressure at introduction of Rb-82-containing solution into the patient.

The process of operation of the strontium-rubidium infusion system takes places under the control from a controlling computer program, which stipulates the condition of every device within the infusion system as of the beginning and the end of a step, as well as actions of the above devices and conditions of their functioning, under normal conditions and in case of emergency.

To prevent overfilling receptacle for eluent and eluate waste 20 with radioactive liquid, there is exercised remote control over the limit value of its level by means of a force sensor, where the overall weight of tare and liquid is controlled, with the liquid weight (volume) value and its limit value monitored. Besides, recording the weight of empty tare for collection of waste, the routine interrogation system of the control and operating unit receives information of the tare's having been placed in the container. The maximum volume of waste in the tare is 250 ml.

The control and operating unit is connected to a remote computer, its display presenting a graphic mnemonic diagram of the generator unit, which ensures observing of monitored parameters in the automatic mode and operative control over particular components (three-way solenoid valves 2-5, pump 10) in the manual mode. The diagram allows observation of the current condition of all the components of the described infusion system (valves 2-5, air bubbles detectors 17, 18) and of operation of syringe pump 10. In addition, it allows obtaining information on parameters of pressure in the lines from pressure sensors 8, 9, activity of eluate at the output of generator column 11 and the aggregate activity, the weight of container of receptacle for eluent and eluate waste 20, and activity in the container with waste from detectors 6, 7.

The system's control and operating unit 12 is connected to operating components of the generator unit—three-way solenoid valves 2, 3, 4, 5 and pump 10, and comprises elements for receiving and processing of signals from sensors 6, 7 (radioactivity sensors), 8, 9 (pressure sensors), 17, 18 (air bubbles detectors). Control and operating unit 12 is connected to panel personal computer (PPC) or any other remote computer (14) via an Ethernet channel. It receives instructions from the PPC, or from the remote computer, on fulfillment of particular steps of the program for operation of the generator unit and informs them on the current condition of components controlled by it and the condition of the system's sensors.

The described systems improves operational safety, as automation of the infusion process has made it possible to considerably reduce nuclear radiation owing to providing the system with additional valves, which ensure ramification of pipelines. It has resulted in a possibility of forcing the rest of generated eluate into the patient, by-passing the strontium-rubidium generator. Here, the pipeline is pumped with non-radioactive eluent, and no additional exhaustion of the strontium-rubidium generator occurs, which extends the latter's service life. Besides, the risk of air bubbles in the eluent delivered to the patient is eliminated owing to the system's being supplemented with air bubbles detectors; with such air bubbles detected, the eluent is fed directly to the receptacle for eluent and eluate waste via the pipeline branches, with no exhaustion caused to the strontium-rubidium generator.

While this invention has been particularly shown and described with references to preferred embodiments thereof, it will be understood by those skilled in the art that various changes in form and details may be made therein without departing from the scope of the invention encompassed by the appended claims.

What is claimed is:

1. An automated strontium-rubidium infusion system comprising:

a first three-way valve comprising a first port, a second port, and a third port, and a second three-way valve comprising a first port, a second port, and a third port;

a syringe pump and an eluent container connected to to the syringe pump via the first port of the first valve and the second port of the first valve;

a strontium-rubidium generator comprising a generator's input and generator's output, a first filter coupled to the generator's input and a first pressure sensor coupled to the generator's input;

means for infusing eluate into a patient, the means for infusing coupled to a second filter and a second pressure sensor for controlling pressure of the eluate infused into the patient;

a control and operating unit connected to a computer and to a third three-way valve comprising a first port, a second port, and a third port and to a fourth three-way valve comprising a first port, a second port, and a third port;

a first air bubbles detector connected to the control and operating unit and disposed along a pipe between the eluent container and the first port of the first valve;

a second air bubbles detector connected to the control and operating unit and disposed along a pipe between the third port of the fourth valve and the third port of the second valve; and means for measuring radioactivity;

wherein the second port of the second valve is connected to a waste receptacle, the first port of the second valve is connected via the pipes and via the second filter to the eluate infusion means, the first port of the third valve is connected via the pipes to the third port of the first valve, the second port of the third valve is connected via the pipes to the input of the generator, the generator's output is connected to the first port of the fourth valve, the third port of the third valve and the second port of the fourth valve are connected with a pipe;

wherein if an amount of strontium-rubidium in the eluate to be delivered to the patient has been generated, or if the first bubble detector detects an air bubble, then the control and operating unit generates a control signal to the third and fourth valves and the eluate bypasses the strontium-rubidium generator;

wherein if the first air bubble detector or the second bubble detector detects an air bubble, then the control and operating unit generates a control signal to the second valve and the eluent solution or the salt solution is removed to the waste receptacle, and wherein if the first bubble detector is activated, the eluent solution is removed to the waste receptacle bypassing the generator.

2. The system according to claim 1, wherein the means for measuring radioactivity comprise a first radioactivity sensor and a second radioactivity sensor for measuring radioactivity of the eluent and the eluate in the waste receptacle and for current control and dosing during infusion into the patient.

3. The system according to claim 2, wherein the first activity sensor is placed on a pipe between the third port of the fourth valve and the third port of the second valve and is a beta-ray detector measuring activity of strontium-rubidium of a dose infused into the patient in real time .

4. The system according to claim 1, wherein the waste receptacle comprises a radiation protection means comprising a protective box, comprising
   a port and
   a waste weight control means comprising
      a force sensor;
wherein the means for measuring radioactivity comprise
a second activity sensor placed in the port of the protective box to determine radioactivity of the waste and comprising a gamma-ray detector.

5. The system according to claim 1, wherein the strontium-rubidium generator comprises radiation protection means, comprising an external primary protective container and
a protective shipping container,
wherein the primary protective container is fixed on a rack of a moving tabletop.

6. The system according to claim 1, further comprising a closed movable housing, wherein the system is installed in the closed movable housing.

7. The system according to claim 6, wherein the housing comprises a sliding tabletop.

* * * * *